US008855749B2

(12) United States Patent
McKenna (10) Patent No.: US 8,855,749 B2
(45) Date of Patent: Oct. 7, 2014

(54) DETERMINATION OF A PHYSIOLOGICAL PARAMETER (75) Inventor: Edward M. McKenna, Boulder, CO (US)

(73) Assignee: Covidien LP, Mansfield, MA (US)

(*) Notice: Subject to any disclaimer, the term of this patent is extended or adjusted under 35 U.S.C. 154(b) by 525 days.

(21) Appl. No.: 12/856,801

(22) Filed: Aug. 16, 2010

(65) Prior Publication Data

US 2011/0071376 A1    Mar. 24, 2011

Related U.S. Application Data (60) Provisional application No. 61/245,575, filed on Sep. 24, 2009.

(51) Int. Cl.
*A61B 6/00* (2006.01)
*G06F 19/00* (2011.01)

(52) U.S. Cl.
USPC ............ 600/473; 600/323; 600/475; 600/476

(58) Field of Classification Search
USPC .................. 600/473, 310, 323, 475, 476, 477
See application file for complete search history.

(56) References Cited

U.S. PATENT DOCUMENTS

| | | | |
|---|---|---|---|
| 3,638,640 A | 2/1972 | Shaw | |
| 4,289,141 A | 9/1981 | Cormier | |
| 4,700,708 A * | 10/1987 | New et al. | 600/331 |
| 4,936,679 A | 6/1990 | Mersch | |
| 4,942,877 A * | 7/1990 | Sakai et al. | 600/323 |
| 4,971,062 A | 11/1990 | Hasebe et al. | |
| 4,974,591 A | 12/1990 | Awazu et al. | |
| 5,028,787 A | 7/1991 | Rosenthal et al. | |
| 5,058,588 A * | 10/1991 | Kaestle | 600/323 |
| 5,065,749 A | 11/1991 | Hasebe et al. | |
| 5,084,327 A | 1/1992 | Stengel | |
| 5,275,159 A | 1/1994 | Griebel | |

(Continued)

FOREIGN PATENT DOCUMENTS

| | | |
|---|---|---|
| JP | 2005095581 | 4/2005 |
| WO | WO9309711 | 5/1993 |

(Continued)

OTHER PUBLICATIONS

PCT International Search Report, Date of mailing Mar. 22, 2011, International application No. PCT/US2010/045572, International filing date Aug. 16, 2010.

(Continued)

*Primary Examiner* — Long V. Le
*Assistant Examiner* — Michael Kellogg
(74) *Attorney, Agent, or Firm* — Fletcher Yoder PC (57) ABSTRACT

Methods and systems are provided for analyzing a physiological signal by applying a continuous wavelet transform on the signal and comparing the wavelet transformation to a library of wavelet signatures corresponding to one or more physiological conditions and/or patient conditions. A pulse oximeter system may relate the wavelet transformation with one or more of the wavelet signatures based on filters and/or thresholds, and may determine that the wavelet transformation indicates that the patient of the physiological signal has a physiological condition indicated by the related wavelet signature. In some embodiments, the pulse oximeter system may use previous analyses in a neural network to update the library. Further, non-physiological components of the wavelet transformation may also be identified and removed.

18 Claims, 7 Drawing Sheets

(56) References Cited

U.S. PATENT DOCUMENTS

| | | |
|---|---|---|
| 5,439,483 A | 8/1995 | Duong-Van |
| 5,483,646 A | 1/1996 | Uchikoga |
| 5,497,769 A | 3/1996 | Gratton et al. |
| 5,590,650 A | 1/1997 | Genova |
| 5,730,124 A | 3/1998 | Yamauchi |
| 5,778,881 A | 7/1998 | Sun et al. |
| 5,779,631 A | 7/1998 | Chance |
| 5,795,304 A | 8/1998 | Sun et al. |
| 5,797,840 A | 8/1998 | Akselrod et al. |
| 5,827,195 A | 10/1998 | Lander |
| 5,830,139 A | 11/1998 | Abreu |
| 5,831,598 A | 11/1998 | Kauffert et al. |
| 5,871,442 A | 2/1999 | Madarasz et al. |
| 5,873,821 A | 2/1999 | Chance et al. |
| 5,957,866 A | 9/1999 | Shapiro et al. |
| 5,967,995 A | 10/1999 | Shusterman et al. |
| 6,002,952 A | 12/1999 | Diab et al. |
| 6,067,462 A | 5/2000 | Diab et al. |
| 6,081,742 A | 6/2000 | Amano et al. |
| 6,095,984 A | 8/2000 | Amano et al. |
| 6,117,075 A | 9/2000 | Barnea |
| 6,120,460 A | 9/2000 | Abreu |
| 6,129,675 A | 10/2000 | Jay |
| 6,134,460 A | 10/2000 | Chance |
| 6,135,966 A | 10/2000 | Ko |
| 6,208,951 B1 | 3/2001 | Kumar et al. |
| 6,285,895 B1 | 9/2001 | Ristolainen et al. |
| 6,293,915 B1 | 9/2001 | Amano et al. |
| 6,312,393 B1 | 11/2001 | Abreu |
| 6,325,761 B1 | 12/2001 | Jay |
| 6,353,750 B1 | 3/2002 | Kimura et al. |
| 6,361,501 B1 | 3/2002 | Taleshi |
| 6,415,236 B2 | 7/2002 | Kobayashi et al. |
| 6,419,671 B1 | 7/2002 | Lemberg |
| 6,461,305 B1 | 10/2002 | Schnall |
| 6,487,439 B1 | 11/2002 | Skladnev et al. |
| 6,519,486 B1 | 2/2003 | Edgar, Jr. et al. |
| 6,544,193 B2 | 4/2003 | Abreu |
| 6,549,795 B1 | 4/2003 | Chance |
| 6,561,986 B2 | 5/2003 | Baura et al. |
| 6,591,122 B2 | 7/2003 | Schmitt |
| 6,606,509 B2 | 8/2003 | Schmitt |
| 6,608,934 B2 | 8/2003 | Scheirer et al. |
| 6,618,042 B1 | 9/2003 | Powell |
| 6,622,095 B2 | 9/2003 | Kobayashi et al. |
| 6,654,623 B1 | 11/2003 | Kastle |
| 6,662,030 B2 | 12/2003 | Khalil et al. |
| 6,675,029 B2 | 1/2004 | Monfre et al. |
| 6,687,519 B2 | 2/2004 | Steuer et al. |
| 6,690,958 B1 | 2/2004 | Walker et al. |
| 6,699,194 B1 | 3/2004 | Diab et al. |
| 6,714,245 B1 | 3/2004 | Ono |
| 6,731,274 B2 | 5/2004 | Powell |
| 6,785,568 B2 | 8/2004 | Chance |
| 6,793,654 B2 | 9/2004 | Lemberg |
| 6,810,277 B2 | 10/2004 | Edgar, Jr. et al. |
| 6,850,053 B2 | 2/2005 | Daalmans et al. |
| 6,898,451 B2 | 5/2005 | Wuori |
| 6,909,808 B2 | 6/2005 | Stanek |
| 6,931,269 B2 | 8/2005 | Terry |
| 6,949,081 B1 | 9/2005 | Chance |
| 6,961,742 B2 | 11/2005 | Neretti et al. |
| 7,020,507 B2 | 3/2006 | Scharf et al. |
| 7,035,679 B2 * | 4/2006 | Addison et al. ............ 600/323 |
| 7,035,697 B1 | 4/2006 | Brown |
| 7,041,063 B2 | 5/2006 | Abreu |
| 7,043,289 B2 | 5/2006 | Fine et al. |
| 7,043,293 B1 | 5/2006 | Baura |
| 7,054,453 B2 | 5/2006 | Causevic et al. |
| 7,054,454 B2 | 5/2006 | Causevic et al. |
| 7,065,392 B2 | 6/2006 | Kato |
| 7,072,702 B2 | 7/2006 | Edgar, Jr. et al. |
| 7,079,888 B2 | 7/2006 | Oung et al. |
| 7,095,491 B2 | 8/2006 | Forstner et al. |
| 7,171,269 B1 | 1/2007 | Addison et al. |
| 7,203,267 B2 | 4/2007 | De Man et al. |
| 7,215,984 B2 | 5/2007 | Diab et al. |
| 7,215,986 B2 | 5/2007 | Diab et al. |
| 7,225,013 B2 | 5/2007 | Geva et al. |
| 7,236,811 B2 | 6/2007 | Schmitt |
| 7,239,902 B2 | 7/2007 | Schmitt et al. |
| 7,254,433 B2 | 8/2007 | Diab et al. |
| 7,254,500 B2 | 8/2007 | Makeig et al. |
| 7,272,426 B2 | 9/2007 | Schmid |
| 7,289,835 B2 | 10/2007 | Mansfield et al. |
| 7,376,453 B1 | 5/2008 | Diab et al. |
| 7,469,158 B2 | 12/2008 | Cutler et al. |
| 7,519,488 B2 | 4/2009 | Fu et al. |
| 7,523,011 B2 | 4/2009 | Akiyama et al. |
| 7,551,950 B2 | 6/2009 | Cheng |
| 7,621,877 B2 | 11/2009 | Schnall |
| 2002/0042558 A1 | 4/2002 | Mendelson |
| 2002/0156354 A1 | 10/2002 | Larson |
| 2002/0183601 A1 | 12/2002 | Tearney et al. |
| 2002/0198443 A1 | 12/2002 | Ting |
| 2003/0023140 A1 | 1/2003 | Chance |
| 2004/0171920 A1 * | 9/2004 | Mannheimer et al. ........ 600/323 |
| 2004/0204637 A1 | 10/2004 | Diab et al. |
| 2005/0033129 A1 | 2/2005 | Edgar et al. |
| 2005/0043763 A1 | 2/2005 | Marcovecchio et al. |
| 2005/0049470 A1 | 3/2005 | Terry et al. |
| 2005/0070774 A1 | 3/2005 | Addison et al. |
| 2005/0113651 A1 | 5/2005 | Wood et al. |
| 2005/0113656 A1 | 5/2005 | Chance |
| 2005/0192488 A1 | 9/2005 | Bryenton et al. |
| 2005/0209517 A1 | 9/2005 | Diab et al. |
| 2005/0228248 A1 | 10/2005 | Dietiker |
| 2006/0009809 A1 | 1/2006 | Marcovecchio et al. |
| 2006/0020181 A1 | 1/2006 | Schmitt |
| 2006/0122475 A1 | 6/2006 | Balberg et al. |
| 2006/0149144 A1 * | 7/2006 | Lynn et al. .................. 600/323 |
| 2006/0155206 A1 | 7/2006 | Lynn et al. |
| 2006/0161071 A1 | 7/2006 | Lynn et al. |
| 2006/0200016 A1 | 9/2006 | Diab et al. |
| 2006/0209631 A1 | 9/2006 | Melese et al. |
| 2006/0211930 A1 | 9/2006 | Scharf et al. |
| 2006/0217609 A1 | 9/2006 | Diab et al. |
| 2006/0229519 A1 | 10/2006 | Fujiwara et al. |
| 2006/0235324 A1 | 10/2006 | Lynn et al. |
| 2006/0247501 A1 | 11/2006 | Ali |
| 2006/0247506 A1 | 11/2006 | Balberg et al. |
| 2006/0258921 A1 | 11/2006 | Addison et al. |
| 2006/0258927 A1 | 11/2006 | Edgar, Jr. et al. |
| 2006/0265022 A1 | 11/2006 | John et al. |
| 2007/0004977 A1 | 1/2007 | Norris et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0129647 A1 | 6/2007 | Lynn et al. |
| 2007/0167694 A1 | 7/2007 | Causevic et al. |
| 2007/0191688 A1 | 8/2007 | Lynn et al. |
| 2007/0191697 A1 | 8/2007 | Lynn et al. |
| 2007/0219059 A1 | 9/2007 | Schwartz et al. |
| 2007/0225581 A1 | 9/2007 | Diab et al. |
| 2007/0249918 A1 | 10/2007 | Diab et al. |
| 2007/0282212 A1 | 12/2007 | Sierra et al. |
| 2007/0291832 A1 | 12/2007 | Diab et al. |
| 2008/0004514 A1 | 1/2008 | Diab et al. |
| 2008/0033266 A1 | 2/2008 | Diab et al. |
| 2008/0036752 A1 | 2/2008 | Diab et al. |
| 2008/0045823 A1 | 2/2008 | Diab et al. |
| 2008/0045832 A1 | 2/2008 | McGrath et al. |
| 2008/0066753 A1 | 3/2008 | Martin et al. |
| 2008/0082018 A1 | 4/2008 | Sackner et al. |
| 2008/0214903 A1 | 9/2008 | Orbach et al. |
| 2011/0071366 A1 | 3/2011 | McKenna |

FOREIGN PATENT DOCUMENTS

| | | |
|---|---|---|
| WO | WO9608992 | 3/1996 |
| WO | WO9842249 | 10/1998 |
| WO | WO9842251 | 10/1998 |
| WO | WO0077675 | 12/2000 |
| WO | WO0077675 A1 | 12/2000 |

(56) References Cited

FOREIGN PATENT DOCUMENTS

| WO | WO0125802 | 4/2001 |
|---|---|---|
| WO | WO0162152 | 8/2001 |
| WO | WO0176461 | 10/2001 |
| WO | WO00182099 | 11/2001 |
| WO | WO0182099 A1 | 11/2001 |
| WO | WO03000125 | 1/2003 |
| WO | WO03055395 | 7/2003 |
| WO | WO2004075746 | 9/2004 |
| WO | WO2004105601 | 12/2004 |
| WO | WO2005096170 | 10/2005 |
| WO | WO2005096931 | 10/2005 |
| WO | WO2006085120 | 8/2006 |
| WO | WO2007131064 | 11/2007 |
| WO | WO2007131066 | 11/2007 |

OTHER PUBLICATIONS

Paul A Leonard et al: "A fully Automated Algorithm for the Determination of Respiratory Rate from the Photoplethysmogram" Journal of Clinical Monitoring and Computing, Kluwer Academic Publishers, DO, vol. 20, No. 1, Feb. 1, 2006, pp. 33-36, XP019250130 ISSN: 1573-2614, the whole document.

Leonard P et al: "Wavelet analysis of pulse oximeter waveforrn permits identification of unwell children." Emergency Medicine Journal: EMJ Jan. 2004 LNKD-PUBMED: 14734378, vol. 21, No. 1, Jan. 2004, pp. 59-60, XP002610773, ISSN: 1472-0213, the whole document.

Salamalekis Emmanuel et al: "Fetal pulse oximetry and wavelet analysis of the fetal heart rate in the evaluation of abnormal cardiotocography tracings." The Journal of Obstetrics and Gynaecology Research Apr. 2006, LNKD-PUBMED: 16594915, vol. 32, No. 2, Apr. 2006, pp. 135-139, XP002610774, ISSN: 1341-8076, the whole document.

Masin, Donald I. et al.; "Fetal Transmission Pulse Oximetry" *Proceedings 19$^{th}$ International Conference IEEE/EMBS* Oct. 30-Nov. 2, 1997; pp. 2326-2329.

Lutter, N. et al.; "Comparison of Different Evaluation Methods for a Multi-wavelength Pulse Oximeter" Biomedizinische Technik vol. 43 (1998).

Rhee, Sokwoo et al.; "Design of a Artifact-Free Wearable Plethysmographic Sensor" Proceedings of the First joint BMES/EMBS Conference Oct. 13-16, 1999 Altanta Georgia p. 786.

Rheineck-Leyssius, Aart t. et al.; "Advanced Pulse Oximeter Signal Processing Technology Compared to Simple Averaging: I. Effect on Frequency of Alarms in the Operating Room" Journal of clinical Anestesia vol. 11 pp. 192-195 (1999).

Tremper, K.K.; "A Second Generation Technique for Evaluating Accuracy and Reliability of Second Generation Pulse Oximeters" Journal of Clinical Monitoring and Computing vol. 16 pp. 473-474 (2000).

Huang, J., et al.; "Low Power Motion Tolerant Pulse Oximetry" *Abstracts* A7 p. S103. (2002).

Jopling, Michael W. et al.; "Issues in the Laboratory Evaluation of Pulse Oximeter Performance" Anesth Analg vol. 94 pp. S62-S68 (2002).

Yamaya, Yoshiki et al.; "Validity of pulse oximetry during maximal exercise in normoxia hypoxia and hyperoxia" J. Appl. Physiol. vol. 92 pp. 162-168 (2002).

Aoyagi, Talmo; "Pulse oximetry: its invention theory and future" Journal of Anesthesia vol. 17 pp. 259-266 (2003).

Johnston, W.S., et al.; "Extracting Breathing Rate Infromation from a Wearable Reflectance Pulse Oximeter Sensor," *Proceedings of the 26$^{th}$ Annual International conference of the IEEE EMBS*, San Francisco, California; Sep. 1-5, 2004; pp. 5388-5391.

Matsuzawa, Y. et al.; "Pulse Oximeter" *Home Care Medicine* pp. 42-45 (Jul. 2004); (Article in Japanese—contains English summary of article).

Pickett, John, et al.; "Pulse Oximetry and PPG Measurements in Plastic Surgery," *Proceedings—19$^{th}$ International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20$^{th}$ Annual International conference of the IEEE Engie in Medicine and Biology Society*, vol. 20, No. 6, p. 3072-3075, 1998.

Todd, Bryan, et al.; "The Identification of Peaks in Physiological Signals," *Computers and Biomedical Research*, vol. 32, pp. 322-335 (1999).

Belal, Suliman Yousef, et al.; "A fuzzy system for detecting distorted plethysmogram pulses in neonates and paediatric patients," *Physiol. Meas.*, vol. 22, pp. 397-412 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Cyrill, D., et al.; "Adaptive Comb Filter for Quasi-Periodic Physiologic Signals," *Proceedings of the 25$^{th}$ Annual International Conference of the IEEE EMBS*, Cancun, Mexico, Sep. 17-21, 2003; pp. 2439-2442.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Spigulis, Janis, et al.; "Optical multi-channel sensing of skin blood pulsations," *Optical Sensing, Proceedings of SPIE*, vol. 5459, pp. 46-53 (2004).

Odagiri, Y.; "Pulse Wave Measuring Device," *Micromechatronics*, vol. 42, No. 3, pp. 6-11 (undated) (Article in Japanese—contains English summary of article).

* cited by examiner

DETERMINATION OF A PHYSIOLOGICAL PARAMETER

RELATED APPLICATION

This application claims the benefit of U.S. Provisional Application No. 61/245,575, filed Sep. 24, 2009, which application is hereby incorporated by reference.

BACKGROUND

The present disclosure relates generally to medical devices and, more particularly, to methods of analyzing physiological parameters using wavelet transforms.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption of the transmitted light in such tissue. A typical pulse oximeter may use light emitting diodes (LEDs) to measure light absorption by the blood. The absorbed and/or scattered light may be detected by the pulse oximeter, which may generate a signal that is proportional to the intensity of the detected light. The received signal may be further processed, and various physiological parameters may be determined based on signal features.

As certain signal features in the signal may be analyzed to determine physiological parameters, it may be beneficial to analyze the signal in a form from which various signal characteristics may be perceived. For example, some signal processing techniques include transforming the signal such that it may be analyzed in the frequency domain. However, such analyses may not provide information that is discernable in the time domain. Methods of processing the signal to perceive various signal characteristics in different domains, and methods of analyzing the processed signal may better enable the identification of physiological conditions based on a physiological signal.

BRIEF DESCRIPTION OF THE DRAWINGS

Advantages of the disclosed techniques may become apparent upon reading the following detailed description and upon reference to the drawings in which.

DETAILED DESCRIPTION

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to determining information from a patient's physiological signal based on a processing and/or comparison of the physiological signal with known signal features. More specifically, a physiological signal is generated by a physiological monitoring system, such as pulse oximeter, in response to light that is detected after being emitted and transmitted through the patient's tissue. The physiological signal may be processed using wavelet transforms to determine various physiological parameters. A wavelet transformation of the physiological signal may enable analyses of certain signal characteristics with respect to both time and frequency. While certain processing techniques or transformations of the physiological signal may result in a globally averaged energy value without information regarding the temporal components of the signal, continuous wavelet transformations may produce information regarding characteristics of the physiological signal (e.g., frequency and/or amplitude) with regard to temporal locations.

The wavelet transformation of the physiological signal, or the wavelet transformed product, may be analyzed for known signal features by comparing the wavelet transformed product to a library of wavelet signatures. Each of the wavelet signatures in the library may correspond to one or more physiological conditions and/or patient characteristics. Signal processing techniques may be utilized to determine whether the wavelet transformed product shares substantially similar characteristics with the wavelet signatures, which may indicate that the patient has the physiological condition correlated with the similar wavelet signature. As wavelet transformed products may enable analyses of multiple dimensions of signal characteristics (e.g., frequency and amplitude with respect to time), comparisons between the wavelet transformed products and the wavelet signatures may also include comparisons of multiple dimensions of signal characteristics. Such multi-dimension analyses and/or comparisons may provide more information for estimating physiological data from the physiological signal, and may enable a more accurate estimation than a comparison of signal characteristics in one dimension. In some embodiments, the probability of a physiological condition may also be produced to indicate the accuracy of the physiological data estimates.

Furthermore, analyses based on wavelet transforms may also involve a supervised learning technique, such as a neural network. For example, previous determinations of physiological conditions may be used to determine physiological conditions in future analyses. In one embodiment, an analysis of a previous wavelet transformed product may have categorized the previous wavelet transformed product as displaying signal characteristics corresponding to a particular physiological condition. Data from the analyses of the previous wavelet transformed product may be used to update the library of wavelet signatures, and/or may be used to form filters for identifying one or more current physiological conditions in analyses of future wavelet transformed products.

Analyzing the wavelet transformed product may also be useful in identifying components in the physiological signal which may be non-physiological and may affect the accuracy of physiological data determined from the signal. For example, various types of noise and interference that may affect the accuracy physiological data estimations may include non-physiological noise sources such as electrical noise, patient motion, or other interferences. Certain non-physiological signal components may be identifiable when amplitude and/or frequency characteristics are analyzed with regard to temporal locations. In some embodiments, the non-physiological signal components may also be removed after they are identified, such that calculations and/or comparisons may be performed on a "clean" wavelet transformed product, improving the likelihood of estimating accurate physiological data.

Figure 1:
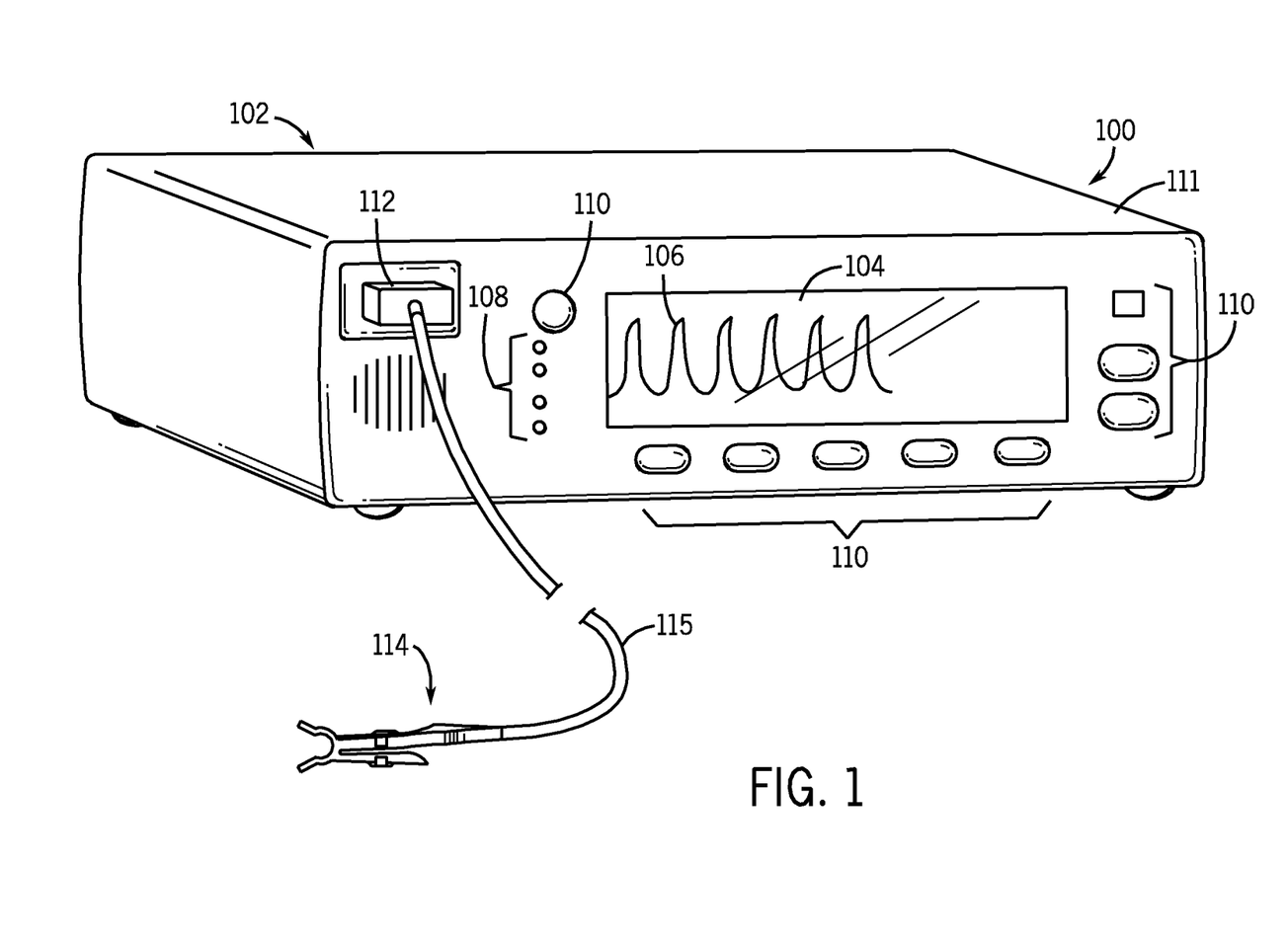
FIG. 1 illustrates a perspective view of a pulse oximeter in accordance with an embodiment.

Turning to FIG. 1, a perspective view of a medical device is illustrated in accordance with an embodiment. The medical device may be a pulse oximeter system 100. The pulse oximeter system 100 may include a monitor 102, such as those available from Nellcor Puritan Bennett LLC. The pulse oximeter system 100 may be utilized to observe the blood constituents of a patient's arterial blood to facilitate estimation of the state of oxygen exchange in the patient's body by emitting light into tissue and detecting the light after dispersion and/or reflection by the tissue. The amount of light that passes through the tissue and other characteristics of the light may vary in accordance with the changing amount of certain blood constituents in the tissue and the related light absorption and/or scattering. As with conventional pulse oximeter systems, the pulse oximeter system 100 may emit light from two or more LEDs or lasers into pulsatile tissue and then detect the transmitted light with a light detector (e.g., a photodiode or photo-detector) after the light has passed through the pulsatile tissue. Such measurements may be utilized to estimate a percentage of blood oxygen saturation in the probed volume of blood.

The monitor 102 may be configured to display calculated parameters on a display 104. As illustrated in FIG. 1, the display 104 may be integrated into the monitor 102. However, the monitor 102 may also be configured to provide data via a port to an external display or secondary monitor. The display 104 may be configured to display computed physiological data including, for example, an oxygen saturation percentage, a pulse rate, and/or a plethysmographic waveform 106. The oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a sensor port 112. The sensor port 112 may allow for connection to an external sensor 114, via a cable 115 which connects to the sensor port 112. The sensor 114 may be of a disposable or a non-disposable type. Furthermore, the sensor 114 may obtain readings from a patient, which can be used by the monitor to calculate certain physiological characteristics such as the blood-oxygen saturation of hemoglobin in arterial blood, the volume of individual blood pulsations supplying the tissue, and/or the rate of blood pulsations corresponding to each heartbeat of a patient.

Figure 2:
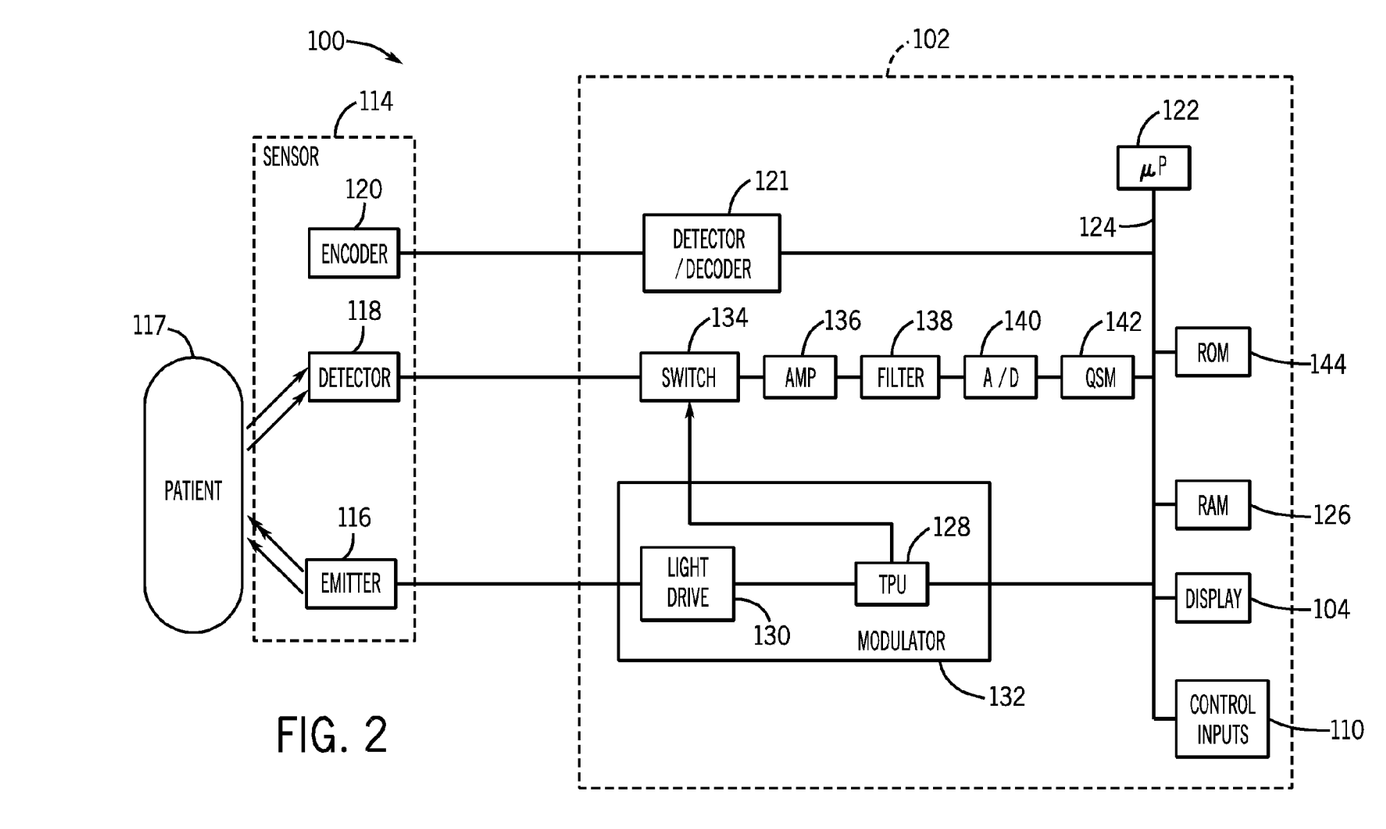
FIG. 2 illustrates a simplified block diagram of a pulse oximeter, according to an embodiment.

Turning to FIG. 2, a simplified block diagram of a pulse oximeter system 100 is illustrated in accordance with an embodiment. Specifically, certain components of the sensor 114 and the monitor 102 are illustrated in FIG. 2. The sensor 114 may include an emitter 116, a detector 118, and an encoder 120. The emitter 116 may receive modulated drive signals from the monitor 102, and may activate and deactivate a light emitting device at certain intervals. For example, the monitor 102 may activate and deactivate components that emit light of different wavelengths, such that light of different wavelength is alternately emitted.

The emitter 116 may be capable of emitting one or more wavelengths of light, e.g., RED and infrared (IR) light, into the tissue of a patient 117, where the RED wavelength may be between about 600 nm and about 700 mm, and the IR wavelength may be between about 800 nm and about 1000 nm. The emitter 116 may include a single emitting device, for example, with two light emitting diodes (LEDs) or the emitter 116 may include a plurality of emitting devices with, for example, multiple LED's at various locations. Regardless of the number of light emitting devices, the emitter 116 may be used to measure, for example, blood oxygen saturation, water fractions, hematocrit, or other physiologic parameters of the patient 117, as discussed herein. It should be understood that, as used herein, the term "light" may refer to one or more of radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use in accordance with the present disclosure.

In one embodiment, the detector 118 may be an array of detector elements that may be capable of detecting light at various intensities and wavelengths. In operation, light enters the detector 118 after passing through the tissue of the patient 117. The detector 118 may convert the light at a given intensity, which may be directly related to the absorbance and/or reflectance of light in the tissue of the patient 117, into an electrical signal. That is, when more light at a certain wavelength is absorbed or reflected, less light of that wavelength is typically received from the tissue by the detector 118. For example, the detector 118 may include one or more photodiodes, or any other element capable of converting light into either a current or voltage. After converting the received light to an electrical signal, the detector 118 may send the signal, which may be a pleth signal, to the monitor 102, where physiological characteristics may be calculated based at least in part on the absorption of light in the tissue of the patient 117.

In some embodiments, the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients for calculating the patient's 117 physiological characteristics. The encoder 120 may, for instance, be a memory on which one or more of the following information may be stored for communication to the monitor 102: the type of the sensor 114; the wavelengths of light emitted by the emitter 116; and the proper calibration coefficients and/or algorithms to be used for calculating the patient's 117 physiological characteristics. In one embodiment, the data or signal from the encoder 120 may be decoded by a detector/decoder 121 in the monitor 102.

Signals from the detector 118 and the encoder 120 may be transmitted to the monitor 102. The monitor 102 may include one or more processors 122 coupled to an internal bus 124. Also connected to the bus 124 may be a RAM memory 126 and a display 104. The monitor 102 may also include a modulator 132, which may include a time processing unit (TPU) 128 and light drive circuitry 130. The modulator 132 may modulate the drive signals that activate the LEDs or other emitting structures of the emitter 116. The modulator 132 may be hardware-based, software-based, or some combination thereof. For example, a software aspect of the modulator 132 may be stored on the memory 126 and may be controlled by the processor 122. The TPU 128 may include a sine wave generator, and may provide timing control signals to light drive circuitry 130, which controls when the emitter 116 is activated, and if multiple light sources are used, the multiplexed timing for the different light sources. TPU 128 may also control the gating-in of signals from detector 118 through a switching circuit 134. These signals are sampled at the proper time, depending at least in part upon which of multiple light sources is activated, if multiple light sources are used.

The received signal from the detector 118 may be processed to provide certain physiological data. In one embodiment, the received signal may be passed through an amplifier 136, a low pass filter 138, and an analog-to-digital converter (ADC) 140 for amplifying, filtering, and digitizing the electrical signals the from the sensor 114. The digital data may then be stored in a queued serial module (QSM) 142, for later downloading to RAM 126 as QSM 142 fills up. There may also be multiple parallel paths for separate amplifiers, filters, and A/D converters for multiple light wavelengths or spectra received. Further, the processor 122 may calculate the oxygen saturation based on the received signals corresponding to the light received by the detector 118. For example, the processor 122 may perform instructions or algorithms stored on the memory 144, and may be configured to perform calculations to estimate physiological parameters based on the received signals.

The processor 122 may also be configured to perform various signal processing operations (e.g., filtering, warping, Fourier transforms, and/or wavelet transforms, etc.) in the estimation of physiological parameters. For example, the processor 122 may apply a wavelet transform to the physiological signal, and the wavelet transformed product may be analyzed to identify a physiological condition and/or identify non-physiological signal components. In some embodiments, the wavelet transformed product may be compared with other wavelet transformations which correspond to various physiological conditions. A table of wavelet transformations may be stored in the RAM 126 or memory 144. Furthermore, the processor 122 may utilize a supervised learning technique, such as a neural network, to identify physiological conditions in a physiological signal.

Figure 3:
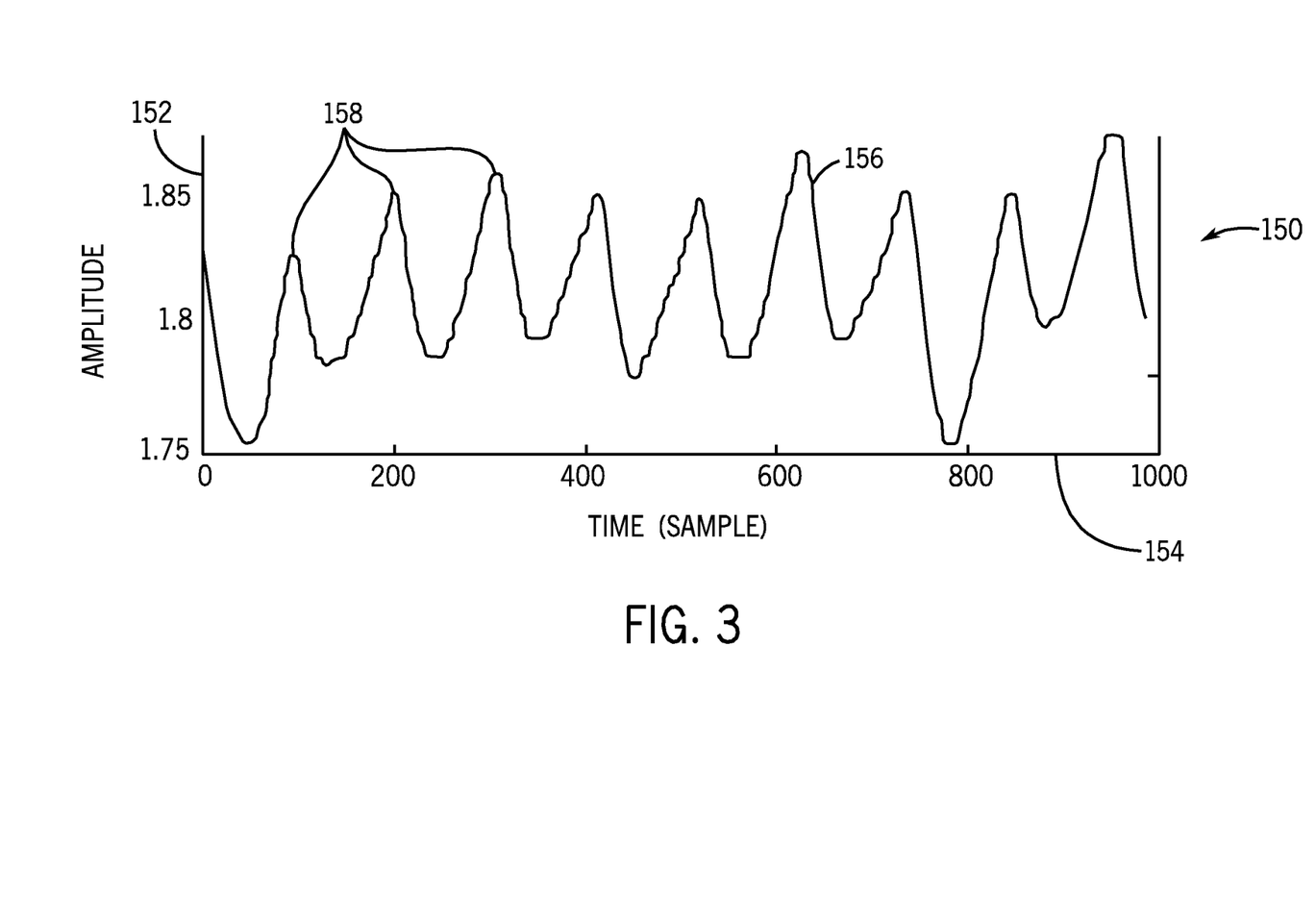
FIGS. 3 and 4 depict, respectively, a graph of physiological signal and a corresponding scalogram resulting from a wavelet transformation of the physiological signal, according to an embodiment.

The graph 150 of FIG. 3, depicts the amplitude 152 over time 154 of a physiological signal 156 which may be generated by a monitor 102 in response to light received at the detector 118 (as in FIG. 2). The physiological signal 156 may be any signal from which may be processed according to the present techniques, and may include information obtainable by emitting various types of waves towards the patient 117, including photon density waves. For example, the physiological signal 156 may include a plethysmographic (pleth) signal or phase change signal (e.g., from a photon density wave).

The physiological signal 156 may be processed to enable the identification of certain physiological parameters of the patient 117. In one embodiment, wavelet transforms may be applied at the monitor 102 to produce an energy map having both time and frequency information. In one embodiment, algorithms or instructions may be implemented or performed by the monitor 102 (e.g., by the processor 122) to transform the physiological signal 156, such that the signals may be analyzed with respect to time, frequency, and/or amplitude. For example, the wavelet transform of a signal x(t) may be defined in the equation below:

$$T(a, b) = \frac{1}{\sqrt{a}} \int_{-\infty}^{+\infty} x(t)\psi^*\left(\frac{t-b}{a}\right)dt \quad \text{eq. (1)}$$

In eq. (1), $\psi^*(t)$ is the complex conjugate of the wavelet function $\psi(t)$. The variable a is the dilation parameter of the wavelet, and b is the location parameter of the wavelet. In one or more embodiments, any suitable wavelet function, including a Morlet wavelet, may be used to obtain a time-frequency representation of the physiological signal 156. The transform of eq. (1) may be regarded as a time-frequency representation where the characteristic frequency associated with the wavelet is inversely proportional to the scale a, and can be used to construct a representation of a signal on a transform surface. The energy density function of the wavelet transform, also referred to as the scalogram, may be defined by the equation below:

$$S_R(a, b) = \frac{|T(a, b)|^2}{a} \quad \text{eq. (2)}$$

where "| |" is the modulus operator. Thus, by applying the wavelet transform on a time-based signal for the time-frequency representation of the signal, and then applying the energy density function of the wavelet transform, a scalogram may be produced. The scalogram, which may also be interpreted as a spectral density of frequency over time, may be a three dimensional model (having time, frequency, and magnitude) from which certain physiological information may be obtained.

Figure 4:
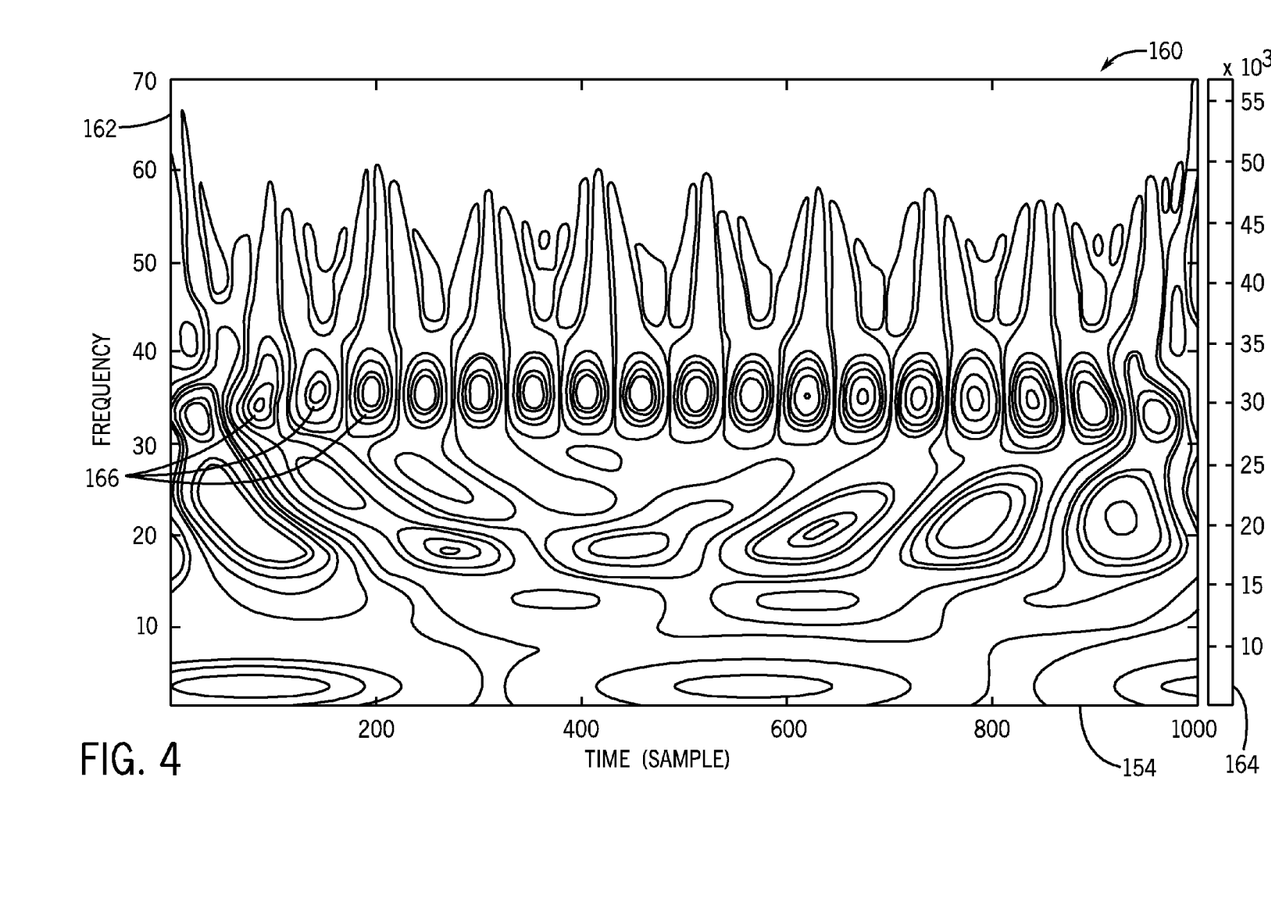

A wavelet transformation of the physiological signal 156 in FIG. 3 is represented as the scalogram 160 in FIG. 4. As discussed, the scalogram 160 may be an example of a wavelet transformed product, and may be a time-frequency representation of the physiological signal 156. The physiological signal 156 and the time-frequency representation of the signal 156 may be represented over the same time 154 in the graph 150 and the scalogram 160. The scalogram 160 may provide a relationship between frequency 162 and amplitude, which may be depicted as a spectral density 164 in the scalogram 160. For example, a spectral range 164 may be used to determine the signal amplitude at any temporal location 154.

Different features may be seen at different frequencies of the scalogram 160, and may match temporally with the original physiological signal 156. For example, changes in amplitude or frequency in the physiological signal 156, such as the amplitude peaks 158, may correspond to certain spectral variations, such as the features 166, in the spectral density 164 of the scalogram 160. The amplitude peaks 158 and/or features 166 in the scalogram 160 may correspond to some physiological parameter (e.g., oxygen saturation, pulse rate, breathing rate, etc.) within a frequency band of the wavelet-transformed signal 156.

Certain features 166 in the scalogram 160, such as patterns, ridges, or spots, may be the locus of points of local maxima in the plane, and may provide information such as amplitude or instantaneous frequency of the signal 156 at that temporal location 154. Thus, both the amplitude (i.e., represented by the spectral density 164), as well as the instantaneous frequency 162 of the physiological signal 156, may be available for any temporal location 154 of the scalogram 160. As some transformations (e.g., a typical Fourier transformation) may return a globally averaged energy value without information regarding the temporal location of signal components, the temporal location of certain signal characteristics may not be available. Thus, applying wavelet transforms may be particularly useful in identifying certain signal features within the physiological signal 156. The identification of certain signal features of the physiological signal 156 through its corresponding scalogram 160 may enable the monitor 102 to better determine various physiological conditions.

Due to the repetitive nature of physiological conditions, a wavelet analysis of a physiological signal enabling analyses with respect for temporal location may used to detect repetition or patterns in a scalogram. Thus, various physiological conditions may be determined by analyzing certain repeated features (e.g., patterns of ridges, spots, etc.). In contrast, noise, motion artifacts, and other non-repetitive phenomena which are not typically characterized by a recurring pattern or signature may be identified as a non-physiological signal component. Thus, various non-physiological components, such as spectral peaks or spikes, may also be identified and resolved (e.g., disregarded, removed, etc.) to produce more accurate data estimates from the physiological signal.

Figure 5:
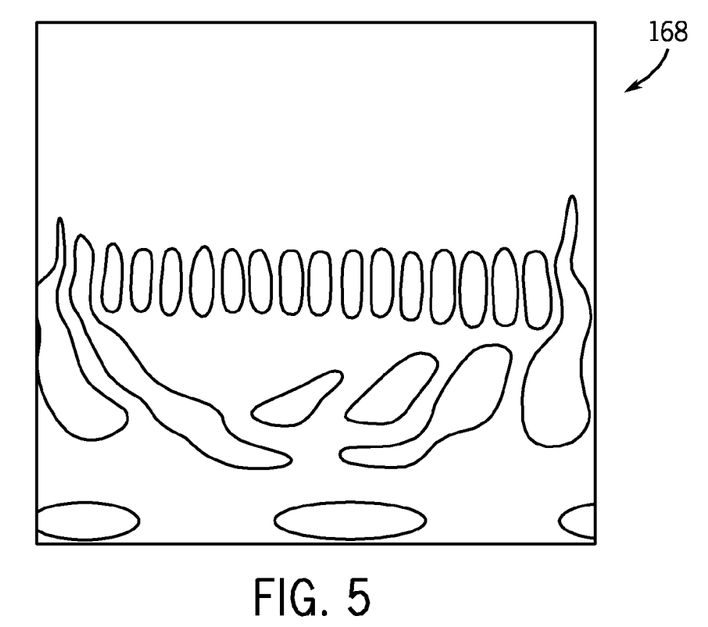
FIGS. 5-7 illustrate a method of comparing the wavelet transformation of a physiological signal to a wavelet transformation of a signal corresponding to a physiological condition, according an embodiment.
Figure 6:
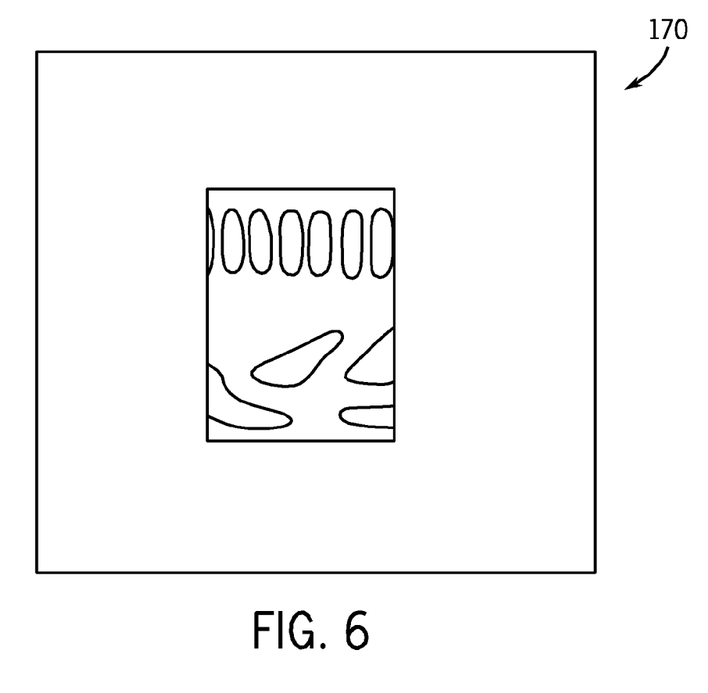
Figure 7:
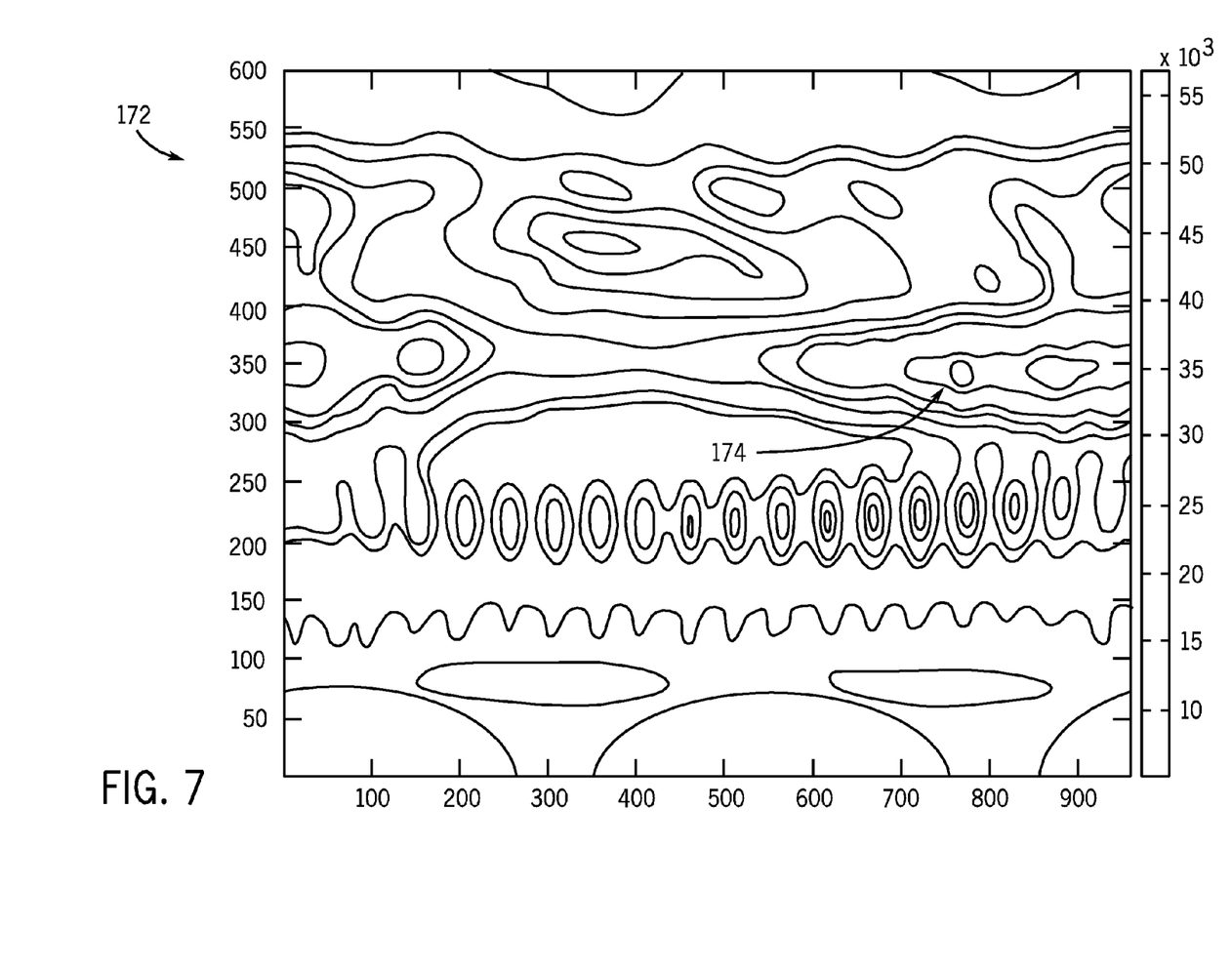

FIGS. 5-7 depict one example of how a pattern indicative of a physiological condition may be detected in a scalogram. In one embodiment, a physiological signal may be processed, such as by applying wavelet transforms, to produce a wavelet transformed product, represented by the scalogram 168 in FIG. 5. The scalogram 168 may be analyzed in view of a wavelet signature 170 (FIG. 6), which may be a wavelet transform or some portion thereof, to determine the presence of some pattern of interest exemplified by the wavelet signature 170. For example, in some embodiments, the scalogram 168 may be cross-correlated with the wavelet signature 170 to determine whether the pattern of interest is present in the scalogram 168. The resulting image 172 (FIG. 7) may represent a cross-correlation of the scalogram 168 with the wavelet signature 170. The identification of some pattern of interest in the scalogram 168 may include setting a threshold spectral intensity for the resulting image 172. Instances in the image 172 that exceed a threshold intensity may indicate that the pattern from the wavelet signature 170 is present in the spectrogram 168. For example, the presence of the depicted darker spot 174 in the image 172 may be used to determine that a pattern from the signature 170 exists in the scalogram 168. Detecting pattern in the scalogram 168 may indicate that the patient of the scalogram 168 has one or more physiological conditions.

The present techniques include analyzing a wavelet transformed physiological signal (e.g., a scalogram) with multiple wavelet signatures, such as the wavelet signature 170 of FIG. 6. Each wavelet signature may be a wavelet transformation of a signal corresponding to a physiological condition. For example, in some embodiments, multiple wavelet signatures may be organized in a library of wavelet signatures and stored in the RAM 126 or the ROM 144 of the monitor 102 (as in FIG. 2). The monitor 102 may utilize various matching or filtering techniques to determine whether a wavelet transformed product shares substantially similar characteristics to any of the wavelet signatures in the library. For example, cross-correlation techniques and/or threshold techniques similar to those described with respect to FIGS. 5-7 may be used for each wavelet signature analysis. When a monitor 102 determines that a wavelet transformed product has a high correlation with a particular wavelet signature, the monitor may categorize the patient 117 from which the signal was generated as having a particular physiological condition.

Furthermore, the monitor 102 may execute a supervised learning technique, such as an artificial neural network, to determine physiological data from a wavelet transformed product. An artificial neural network may be used to represent or process nonlinear functions, such as a wavelet transformed product, and apply and/or analyze the wavelet transformed product with a large data set, such as a library of wavelet signatures. The artificial neural network engine may be data processing architecture which may be implemented in software, hardware, or a combination of both. Further, the artificial neural network may be executed by the processor 122, an external computer system coupled to the monitor 102, or by hardware of the monitor 102 (not illustrated). In some embodiments, a supervised learning technique may involve utilizing a previously analyzed wavelet transformed physiological signal to update a library of wavelet signatures.

Figure 8:
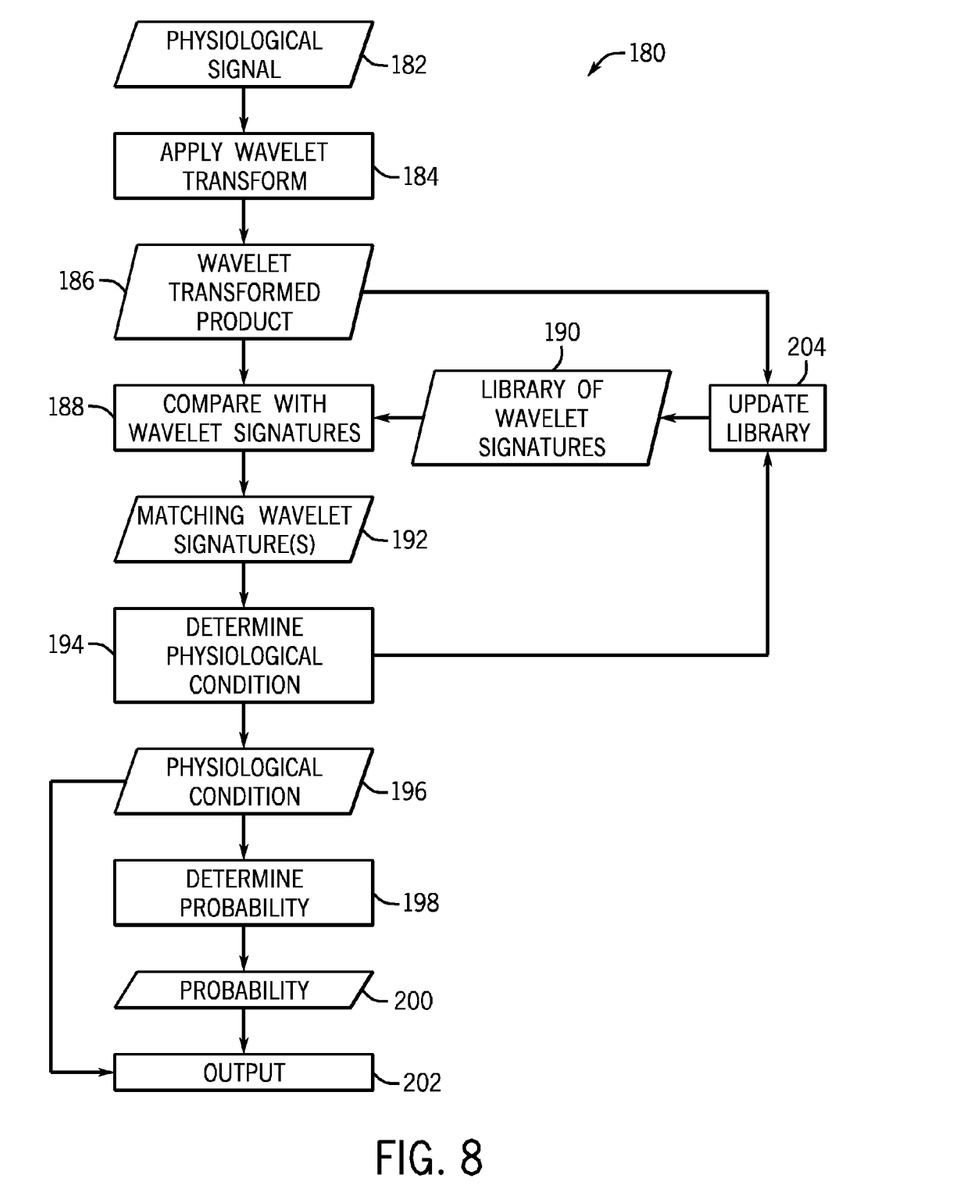
FIG. 8 is a flow chart of a method for determining a physiological condition based on a wavelet transformation of a physiological signal, according to an embodiment.

Determining a physiological condition based on a wavelet transformation of a physiological signal and a comparison of the wavelet transformed signal with multiple wavelet signatures may be depicted in the flow chart 180 of FIG. 8. As discussed, a physiological signal 182 may be generated in response to an intensity of light received at a detector 118 of a pulse oximeter sensor 114 (as in FIGS. 1 and 2). The monitor 102 may process the physiological signal 182 by applying wavelet transforms (block 184) to produce a wavelet transformed product 186 that is a representation of the physiological signal 182 in time and frequency domains. For example, the wavelet transformed product 186 may be represented in a scalogram (as in FIGS. 4 and 5). The monitor 102 may then analyze the wavelet transformed product 186 to determine physiological data.

The monitor 102 may analyze the wavelet transformed product 186 by comparing the product 186 with a library 190 of wavelet signatures 170 (block 188). Each of the wavelet signatures 170 may be a wavelet transformation having features and/or patterns which correspond to a particular physiological condition. Furthermore, the wavelet signatures 170 may be categorized in the library 190 based on patient characteristics such as gender, age, weight, or diagnosis, or characteristics of the pulse oximeter 100, including sensor type, sensor placement, etc. The categorization of wavelet signatures may enable the monitor 102 to compare the wavelet transformed product 186 with the most relevant wavelet signatures in the library 190. For example, the monitor may determine which of the wavelet signatures 170 in the library 190 have similar patient characteristics as the patient and similar sensor specifications as the sensor measuring the physiological signal 182. The monitor 102 may then determine whether the any of these wavelet signatures 170 share substantially similar characteristics (e.g., patterns of scalogram features such as ridges or spots) with the wavelet transformed product 186. While in some embodiments, the monitor 102 may perform a comparison of the wavelet transformed product 186 with all the wavelet signatures 170 in the library 190, in other embodiments, limiting the comparisons to categories of similar wavelet signatures 170 may reduce processing power.

The comparison of the wavelet transformed product 186 and the wavelet signatures 170 (block 188) may be performed through cross-correlating the wavelet transformed product 186 with one or more wavelet signatures 170, as previously discussed with respect to FIGS. 5-7. The resulting cross-correlated images may be filtered to determine whether a matching wavelet signature 192 is present. A matching wavelet signature 192 may have similar characteristics as the wavelet transformed product 186, or may meet a threshold level of correlation. The monitor 102 may then use the matching wavelet signature 192 to determine the physiological condition of the patient (block 194). The monitor 102 may determine that the patient has one or more physiological conditions 196 corresponding to the matching wavelet signatures 192.

In some embodiments, the monitor 102 may also determine the probability (block 198) that the physiological condition 196 determined for the patient is accurate. Probability may be determined, for example, based on a level of correlation or a degree of similarity between the wavelet transformed product 186 and the matching signature 192. In one embodiment, determining the probability (block 198) may also include evaluating and ranking multiple physiological conditions 196, such that the patient may have more information on possible and/or likely physiological conditions 196. The probability 200 and/or the physiological condition(s) 196 may be output (block 202) by the monitor 102, for example, via the display 104.

The display of the physiological condition(s) 196 may include physiological data, such as a patient's heart rate, oxygen saturation, or any other monitored statistic or data. The display of physiological condition(s) 196 may also include recommendations regarding a condition of the patient or the measurement of data. For example, the recommendations may include alerts to a caregiver, such as if the patient's diagnoses requires immediate attention. Recommendations may also be displayed to improve the quality of physiological data. For example, if the position of the sensor or the movement of the patient is causing an inaccurate measurement of the physiological signal 182, thus resulting in a low probability 200, the monitor 102 may display recommendations on how to improve the probability 200 and the accuracy of estimating physiological conditions 196. Such diagnoses and/or recommendations may be organized on the display 104 based on the likelihood that the diagnoses or recommendations are accurate. Furthermore, in some embodiments, the display of physiological condition(s) may also include a diagnosis, such as a specific condition or disease (e.g., arrhythmia), as well as a probability 200 of the accuracy of the diagnosis.

As discussed, supervised learning techniques may also be implemented in accordance with the present techniques. In one embodiment, the monitor 102 may update the library 190 (block 204) after determining the physiological condition 196 of the patient. Updating the library (block 204) may include storing data of the analysis of a current wavelet transformed product 186 in the library 190, such that future analyses of the wavelet transformed product 186 may be based on an updated library 190. For example, the monitor may categorize the current wavelet transformed product 186 based on the patient characteristics (e.g., age, gender, diagnosis, etc.) and the determined physiological condition 196. Thus, in future analyses, the monitor may access wavelet signatures 170 specific to the current patient, or specific to a patient having similar characteristics. Such techniques may result in a higher probability 200 that the monitor 102 may estimate an accurate physiological condition 196, as the updated wavelet transformed product may have a higher correlation with future wavelet transformed products. This may result in higher confidence diagnoses of a patient based on the patient's wavelet transformed physiological signal.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A method for assessing a plethysmography signal to provide an output related to a physiological condition, comprising using a processor of a pulse oximeter monitor to perform the steps of:
    receiving the plethysmography signal from a pulse oximeter sensor applied to a patient, wherein the pulse oximeter sensor comprises an encoder configured to transmit information indicative of a type of the pulse oximeter sensor to the pulse oximeter monitor;
    processing the plethysmography signal using a continuous wavelet transform;
    comparing a result of the continuous wavelet transform to a library comprising a plurality of wavelet signatures, the plurality of wavelet signatures comprising previously-determined patterns that correspond to physiological conditions and being categorized based on characteristics of a pulse oximeter system;
    identifying one or more wavelet signatures of the plurality of wavelet signatures in the library that have sensor specifications similar to the pulse oximeter sensor, wherein comparing the result comprises comparing the result to the one or more identified wavelet signatures to determine the physiological condition of the patient; and
    displaying the output related to the physiological condition of the patient.

2. The method, as set forth in claim 1, wherein the wavelet transform comprises a Morlet wavelet.

3. The method, as set forth in claim 1, wherein the output related to the physiological condition comprises one or more of a diagnosis, a first recommendation comprising an alert, or a second recommendation for improving a measurement of the physiological signal.

4. The method, as set forth in claim 1, wherein the different respective physiological conditions comprise one or more disease states.

5. The method, as set forth in claim 1, wherein comparing the result comprises filtering the result to determine whether the result meets a threshold level of correlation with the one or more identified wavelet signatures of the plurality of wavelet signatures in the library.

6. The method, as set forth in claim 1, wherein comparing the result comprises deriving a correlation value between the result and the one or more identified wavelet signatures of the plurality of wavelet signatures in the library.

7. The method, as set forth in claim 1, comprising:
utilizing the result and the determined physiological condition in a learning based algorithm; and
updating the library based on the result, the determined physiological condition, and the learning based algorithm, wherein comparing the result comprises comparing the continuous wavelet transform to the updated library.

8. The method, as set forth in claim 1, wherein the result of the continuous wavelet transform comprises a scalogram comprising a spectral density of the signal with respect to frequency and time.

9. A method for assessing a plethysmography signal to provide an output related to a physiological condition, comprising using a processor of a pulse oximeter monitor to perform the steps of:
receiving the plethysmography signal from a pulse oximeter sensor applied to a patient, wherein the pulse oximeter sensor comprises an encoder configured to provide information indicative of the type of pulse oximeter sensor to the pulse oximeter monitor;
processing the plethysmography signal using a continuous wavelet transform;
accessing a plurality of wavelet signatures comprising previously determined features that correspond to a plurality of physiological conditions;
identifying one of more wavelet signatures of the plurality of wavelet signatures that have a sensor type similar to the pulse oximeter sensor;
comparing a result of the continuous wavelet transform to the one or more identified wavelet signatures to determine a physiological condition of the patient; and
displaying the output related to the physiological condition of the patient.

10. The method, as set forth in claim 9, wherein the wavelet transform comprises a Morlet wavelet.

11. The method, as set forth in claim 9, wherein the output related to the physiological condition comprises one or more of a diagnosis, a first recommendation comprising an alert, or a second recommendation for improving a measurement of the physiological signal.

12. The method, as set forth in claim 9, wherein the plurality of physiological conditions comprise one or more disease states.

13. The method, as set forth in claim 9, wherein the result of the continuous wavelet transform comprises a scalogram comprising a spectral density of the signal with respect to frequency and time.

14. The method, as set forth in claim 9, comprising updating the library based on one or more of the result or the determined physiological condition.

15. The method, as set forth in claim 9, wherein comparing the result comprises:
cross-correlating the result with a wavelet signature to produce a cross-correlated image; and
determining whether the result meets a threshold level of correlation with the wavelet signature based on the cross-correlated image.

16. The method, as set forth in claim 15, wherein determining whether the result meets the threshold level of correlation is based on comparing a spectral intensity of the cross-correlated image to a threshold intensity.

17. The method, as set forth in claim 9, wherein comparing the result comprises filtering the result to determine whether the result meets a threshold level of correlation with the wavelet signature.

18. The method, as set forth in claim 1, wherein the characteristics of the pulse oximeter system comprise one or more of a sensor type or a sensor placement.

* * * * *